(12) United States Patent
Zigdon-Giladi et al.

(10) Patent No.: US 9,168,139 B2
(45) Date of Patent: Oct. 27, 2015

(54) VERTICAL BONE AUGMENTATION USING ENDOTHELIAL PROGENITOR CELLS

(71) Applicants: Hadar Zigdon-Giladi, Haifa (IL); Dina Lewinson, Haifa (IL); Tova Bick, Haifa (IL); Eli Machtei, Haifa (IL)

(72) Inventors: Hadar Zigdon-Giladi, Haifa (IL); Dina Lewinson, Haifa (IL); Tova Bick, Haifa (IL); Eli Machtei, Haifa (IL)

(73) Assignee: Health Corporation—Rambam (IL)

( * ) Notice: Subject to any disclaimer, the term of this patent is extended or adjusted under 35 U.S.C. 154(b) by 90 days.

(21) Appl. No.: 13/918,602

(22) Filed: Jun. 14, 2013

(65) Prior Publication Data

US 2013/0282139 A1   Oct. 24, 2013

Related U.S. Application Data

(63) Continuation of application No. PCT/IB2011/003059, filed on Dec. 15, 2011.

(60) Provisional application No. 61/423,120, filed on Dec. 15, 2010.

(51) Int. Cl.
| | | |
|---|---|---|
| A61F 2/28 | (2006.01) | |
| A61L 27/12 | (2006.01) | |
| A61L 27/22 | (2006.01) | |
| A61L 27/24 | (2006.01) | |
| A61L 27/38 | (2006.01) | |
| C12N 5/0775 | (2010.01) | |
| C12N 5/071 | (2010.01) | |

(52) U.S. Cl.
CPC . *A61F 2/28* (2013.01); *A61L 27/12* (2013.01); *A61L 27/225* (2013.01); *A61L 27/24* (2013.01); *A61L 27/3808* (2013.01); *A61L 27/3821* (2013.01); *A61L 27/3847* (2013.01); *C12N 5/0663* (2013.01); *C12N 5/0668* (2013.01); *C12N 5/0692* (2013.01); *C12N 2533/54* (2013.01); *C12N 2533/80* (2013.01)

(58) Field of Classification Search
CPC ......... A61F 2/30767; A61F 2/36; A61F 2/28; A61F 2002/30677
USPC .................................. 623/16.11, 23.51–23.61
See application file for complete search history.

(56) References Cited

U.S. PATENT DOCUMENTS

| | | | |
|---|---|---|---|
| 2007/0156251 A1* | 7/2007 | Karmon | ..................... 623/23.61 |
| 2008/0033548 A1 | 2/2008 | Xuenong et al. | |
| 2008/0125863 A1 | 5/2008 | McKay | |
| 2008/0147197 A1 | 6/2008 | McKay | |
| 2010/0003222 A1 | 1/2010 | Yayon et al. | |

(Continued)

FOREIGN PATENT DOCUMENTS

WO           0035510 A1      6/2000

OTHER PUBLICATIONS

Augello et al., (2010) Mesenchymal stem cells: a perspective from in vitro cultures to in vivo migration and niches. Eur Cell Mater 20: 121-33.

(Continued)

*Primary Examiner* — Jason-Dennis Stewart
(74) *Attorney, Agent, or Firm* — Whitmyer IP Group LLC (57) ABSTRACT

A method of facilitating augmentation of osseous tissue on a surface of a bone is disclosed. The method includes combining a scaffolding, an enclosure substantially enclosing the scaffolding relatively to the surface of the bone and a cell culture seeded onto the scaffolding.

17 Claims, 4 Drawing Sheets

(56) References Cited

U.S. PATENT DOCUMENTS

2010/0172863 A1  7/2010  Wasielewski
2011/0313538 A1* 12/2011  Oh et al. ............ 623/23.61

OTHER PUBLICATIONS

Kaigler et al., (2010) Angiogenic and osteogenic potential of bone repair cells for craniofacial regeneration. Tissue Eng Part A 16(9): 2809-20.
Ward et al., (2010) Bioengineering strategies for regeneration of craniofacial bone: a review of emerging technologies. Oral Dis 16(8): 709-16.
Albandar (1990) Some predictors of radiographic alveolar bone height reduction over 6 years. J Periodontal Res 25(3): 186-92.
Arairjo and Lindhe (2009) Ridge preservation with the use of Bio-Oss collagen: aA6-month study in the dog. Clin Oral Implants Res 20(5): 433-40.
Artzi et al., (2001) Porous bovine bone mineral in healing of human extraction sockets: 2. Histochemical observations at 9 months. J Periodontol 72(2): 152-9.
Banfi et al., (2000) Proliferation kinetics and differentiation potential of ex vivo expanded human bone marrow stromal cells: Implications for their use in cell therapy. Exp Hematol 28(6): 707-15.
Bick et al., (2006) Osteogenic differentiation of circulating endothelial progenitor cells. J of Bone and Min Res 22: S143.
Bruder et al., (1998) The effect of implants loaded with autologous mesenchymal stem cells on the healing of canine segmental bone defects. J Bone Joint Surg Am 80(7): 985-96.
Camelo et al., (1998) Clinical, radiographic, and histologic evaluation of human periodontal defect treated with Bio-Oss and Bio-tide. Int J Periodontics Restorative Dent 18(4): 321-31.
Cetrulo et al., (2005) Stem cells and distraction osteogenesis: endothelial progenitor cells home to the ischemic generate in activation and consolidation. Plast Reconstr Surg 116(4): 1053-64.
Chiapasco et al., (2006) Augmentation procedures for the rehabilitation of deficient edentulous ridges with oral implants. Clin Oral Implants Res 17 Suppl 2: 136-59.
Dahlin et al., (1988) Healing of bone defects by guided tissue regeneration. Plast Reconstr Surg 81(5): 672-6.
Dahlin et al., (1990) Healing of maxillary and mandibular bone defects using a membrane technique. An experimental study in monkeys. Scand J Plast Reconstr Surg Hand Surg 24(1): 13-9.
Donos et al., (2004) Effect of GBR in combination with deproteinized bovine bone mineral and/or enamel matrix proteins on the healing of critical-size defects. Clin Oral Implants Res 15(1): 101-11.
Esposito et al., (2006) The efficacy of various bone augmentation procedures for dental implants: a Cochrane systematic review of randomized controlled clinical trials. Int J Oral Maxillofac Implants 21(5): 696-710.
Friedenstein et al., (1966) Osteogenesis in transplants of bone marrow cells. J Embryol Exp Morphol 16(3): 381-90.
Fuchs et al., (2009) Dynamic processes involved in the pre-vascularization of silk fibroin constructs for bone regeneration using outgrowth endothelial cells. Biomaterials 30(7): 1329-38.
Giannoudis et al., (2007) Fracture healing: the diamond concept. Injury 38 Suppl 4: S3-6.
Greenstein et al., (2009) The role of bone decortication in enhancing the results of guided bone regeneration: a literature review. J Periodontol 80(2): 175-89.
Gregory et al., (2005) Non-hematopoietic bone marrow stem cells: molecular control of expansion and differentiation. Exp Cell Res 306(2): 330-5.
Haney et al., (1993) Periodontal repair in dogs: expanded polytetrafluoroethylene barrier membranes support wound stabilization and enhance bone regeneration. J Periodontol 64(9): 883-90.
Horwitz et al., (2002) Isolated allogeneic bone marrow-derived mesenchymal cells engraft and stimulate growth in children with osteogenesis imperfecta: Implications for cell therapy of bone. Proc Natl Acad Sci U S A 99(13): 8932-7.
Irinakis (2006) Rationale for socket preservation after extraction of a single-rooted tooth when planning for future implant placement. J Can Dent Assoc 72(10): 917-22.
Jafarian et al., (2008) Marrow-derived mesenchymal stem cells-directed bone regeneration in the dog mandible: a comparison between biphasic calcium phosphate and natural bone mineral. Oral Surg Oral Med Oral Pathol Oral Radio! Endod 105(5): e14-24.
Kalka et al., (2000) Transplantation of ex vivo expanded endothelial progenitor cells for therapeutic neovascularization. Proc Natl Acad Sci U S A 97(7): 3422-7.
Khojasteh et al., (2008) Mesenchymal stem cells enhance bone regeneration in rat calvarial critical size defects more than platelete-rich plasma. Oral Surg Oral Med Oral Pathol Oral Radio! Endod 106(3): 356-62.
Kim and Kim (2008) Comparison of osteogenic potential between apatite-coated poly lactide-co-glycolide / hydroxyapatite particulates and Bio-Oss. Dent Mater J 27(3): 368-75.
Kostopoulos and Karring (1994) Augmentation of the rat mandible using guided tissue regeneration. Clin Oral Implants Res 5(2): 75-82.
Kostopoulos et al., (1994) Formation of jawbone tuberosities by guided tissue regeneration. An experimental study in the rat. Clin Oral Implants Res 5(4): 245-53.
Lang et al., (2003) Alveolar Bone Formation. In: Lindhe J, Karring T & Lang NP, Editors. Clinical periodontology and implant dentistry. Fourth edition. Blackwell Munksgaard,: pp. 870-873.
Lee et al., (2008) Mobilization of endothelial progenitor cells in fracture healing and distraction osteogenesis. Bone 42 (5): 932-41.
Lioubavina et al., (1999) Long-term stability of jaw bone tuberosities formed by "guided tissue regeneration". Clin Oral Implants Res 10(6): 477-86.
Lundgren et al., (1995) Augmentation of intramembraneous bone beyond the skeletal envelope using an occlusive titanium barrier.An experimental study in the rabbit. Clin Oral Implants Res 6(2): 67-72.
Lundgren et al., (2000) Influence of decortication of the donor bone on guided bone augmentation. An experimental study in the rabbit skull bone. Clin Oral Implants Res 11(2): 99-106.
Machtei (2001) the effect of membrane exposure on the outcome of regenerative procedures in humans: a meta-analysis. J Periodontol 72(4): 512-6.
Nyman et al., (1987) New attachment formation by guided tissue regeneration. J Periodontal Res 22(3): 252-4.
Petite et al., (2000) Tissue-engineered bone regeneration. Nat Biotechnol 18(9): 959-63.
Piattelli et al., (1999) Bone reactions to anorganic bovine bone (Bio-Oss) used in sinus augmentation procedures: a histologic long-term report of 20 cases in humans. Int J Oral Maxillofac Implants 14(6): 835-40.
Pitaru et al., (1987) Collagen membranes prevent the apical migration of epithelium during periodontal wound healing. J Periodontal Res 22(4): 331-3.
Quarto et al., (2001) Repair of large bone defects with the use of autologous bone marrow stromal cells. n. Engl J Med 344(5): 385-6.
Rocchietta et al., (2008) Clinical outcomes of vertical bone augmentation to enable dental implant placement: a systematic review. J Clin Periodontol 35(8 Suppl): 203-15.
Rojbani et al., (2011) Evaluation of the osteoconductivity of α-tricalcium phosphate, β-tricalcium phosphate, and hydroxyapatite combined with or without simvastatin in rat calvarial defect. J. Biomid Mater Res A 98(4): 488-98.
Rothamel et al., (2009) Vertical ridge augmentation using xenogenous bone blocks: a histomorphometric study in dogs. Int J Oral Maxillofac Implants 24(2): 243-50.
Rozen et al., (2009) Transplanted blood-derived endothelial progenitor cells (EPC) enhance bridging of sheep tibia critical size defects. Bone 45(5): 918-24.
Slotte and Lundgren (1999) Augmentation of calvarial tissue using non-permeable silicone domes and bovine bone mineral. An experimental study in the rat. Clin Oral Implants Res 10(6): 468-76.
Valentini et al., (1998) Histological evaluation of Bio-Oss in a 2-stage sinus floor elevation and implantation procedure. A human case report. Clin Oral Implants Res 9(1): 59-64.

(56) References Cited

OTHER PUBLICATIONS

Verna et al., (2002) Healing patterns in calvarial bone defects following guided bone regeneration in rats. A micro-CT scan analysis. J Clin Periodontol 29(9): 865-70.

Zhou et al., (2008) Age-related intrinsic changes in human bone-marrow-derived mesenchymal stem cells and their differentiation to osteoblasts. Aging Cell 7(3): 335-43.

Zuk et al., (2001) Multilineage cells from human adipose tissue: implications for cell-based therapies. Tissue Eng 7(2): 211-28.

* cited by examiner

VERTICAL BONE AUGMENTATION USING ENDOTHELIAL PROGENITOR CELLS

FIELD OF THE INVENTION

In general, the present invention pertains to the arts of medicine. In particular, the invention relates to a bone augmentation systems and methods, employing endothelial progenitor cells and scaffolding.

BACKGROUND OF THE INVENTION

Alveolar bone atrophy may occur due to trauma, malignant tumors, and periodontal disease (Albandar 1990, Schwartz-Arad & Levin 2004, Irinakis 2006). Restoring the lost bone is crucial for the rehabilitation of the patient's function, phonetics and aesthetic demands.

Nowadays, the methods available for vertical bone augmentation include: distraction osteogenesis, bone blocks (autologic/allogenic or xenogenic) and guided bone regeneration (GBR). These techniques are surgically complicated, unpredictable and some of them are also associated with significant morbidity (Chiapasco et al. 2006, Rothamel et al. 2009, Greenstein et al. 2009, Esposito et al. 2006, Rocchietta et al. 2008). The idea of using a physical barrier for guided bone regeneration (GBR) was first described in the early 80's by Nyman et al (Nyman et al. 1982a, Nyman et al. 1982b, Nyman et al. 1987, Pitaru et al. 1987). It was demonstrated that creating a critical size intra bony defect and covering the defect with mucoperiosteal flap will lead to healing of the defect, mostly with soft tissue; while when a barrier to separate the bone defect from the soft tissue is used, it allows for bone regeneration into the defect (Dahalin et al. 1990, Kostopoulos et al. 1994a, Kostopoulos et al. 1994b, Dahalin et al. 1988). The biological principle of GBR also includes the creation of a space between a rigid barrier and the underlying bone which prevents epithelial and fibroblastic cells migration from the soft tissue, thus enabling the slower moving bone-forming cells to migrate from the underlying bone to populate the space (Polimeni et al. 2005, Schenk et al. 1994). Another important role of the membrane is blood clot stabilization. It was demonstrated that supra-crestal bone defects that were treated with ePTFE membrane and had root conditioning with heparin, showed compromised periodontal healing and bone regeneration (Haney et al. 1993).

As of today, bone regeneration within the bony envelope (intra-bony) using GBR technique is a common and relatively predictable procedure (Kim et al. 2004). However, only few studies that attempted to grow bone extra cortically using C3B resulted with modest success (Majzoub et al. 1999, Min et al. 2007, Lundgren et al. 1995, Wikesjo et al. 2003, Lioubavina & Kostopoulos 1999).

Both the calvaria and the jaw bones are formed through the intra-membranous bone formation pathway (Verna et al. 2002). The process begins with the proliferation of mesenchymal cells and deposition of extracellular matrix. This newly formed tissue guides cell migration and angiogenesis. The combination of matrix components with new vessels forms provisional connective tissue that is later transformed into bone along blood vessels (Lang et al. 2003).

Mesenchymal stem cells (MSC) contribute to the maintenance of various tissues, especially bone, in adults. They can be isolated form bone marrow, placenta, umbilical cord blood, or from adipose tissue in adults (Pittenger et al. 1999, Secco et al. 2008, Zuk et al. 2001, Yen et al. 2005). The first to describe these cells was Friedenstein in 1966. MSC present several characteristics that assist to identify them: adherence to culture plates, fibroblast-like phenotype and proliferation potential. The osteogenic potential of these cells was also recognized (Friedenstein). Since that time, in-vivo and in-vitro studies showed that MSC can be transformed into mesenchymal tissues such as: bone, cartilage, adipose, muscle and tendon. The characterization of cultured MSC relies on combination of several antigens: CD105, CD146, CD90, CD73 and CD44; furthermore, the hematopoietic origin of the cells should be excluded (CD45, CD14 and CD34) (Baksh 2004, Geregory et al. 2005).

Several preclinical studies and a few clinical studies showed the efficacy of cultured MSC for bone reconstruction. In animal models these cells showed osteoinductive properties (i.e production of ectopic bone) and improved healing of bone defects (Petite et al. 2000, Bruder et al. 1998). In humans, few clinical reports (case reports) were published: Quarto et al. 2001 reported on callus formation 2 months after administration of autologous MSC seeded on hydroxyapatite scaffold into non-union long bone defects. The I.V. infusion of autologous MSC to children with osteogenesis imperfecta resulted in increase in their body length and bone mineral content (Horowits et al. 2002).

Several attempts to heal mandibular defect in animals using MSC have also been recently published. These studies reported that the addition of MSC to scaffold have statistically improved bone regeneration compared with scaffold alone (Steinhardt et al. 2008, Jafarian et al. 2008).

Although extensively studied, several difficulties concerning the use of bone marrow MSC still exist. The main problems are the invasive nature associate with the harvesting of MSC and the morbidity of the donor. Additionally some reports suggest age-dependent decline in the proliferation and the osteogenic differentiation of these cells (Zhou et al. 2008). Finally, the limited amount of MSC in bone marrow aspirates requires ex-vivo expansion to obtain sufficient cell number for transplantation (Banfi et al. 2000). Thus, extensive research to improve our laboratory techniques and control clinical trials is still needed in order to confirm the potential of MSC to induce new bone formation.

Blood-derived endothelial progenitor cells (EPC)—In 1997, Asahara et al. discovered the presence of bone marrow-derived circulating endothelial progenitor cells in adult peripheral blood and human umbilical cord blood (Ashara et al. 1997, Murohara et al. 2000) that participate in post-natal neovascularization (Takahashi et al. 1999). Furthermore, these cell lines were found to participate in angiogenesis, vascular repair, blood-flow recovery after tissue ischemia and vasculoprotection. The current clinical use of EPC is limited to treating ischemic tissue after acute myocardial infarct (Isner & Losordo 1999, Kalka et al. 2000). During skeletal development or bone healing processes the recruitment of EPC by vasculogenic/angiogenic molecules (e.g. VEGF, PlGF, erythropoietin) is crucial (Ferguson et al. 1999, Giannoudis et al. 2007). Studies that explored the effect of local delivery of BMP2 & VEGF loaded on scaffold on bone regeneration suggest a synergistic effect in this dual delivery system (Patel et al. 2008, Kempen et al. 2009). Dual release of BMP2 & VEGF from scaffold implanted into calvaria-bone defect in rats enhanced bone formation after 4 weeks compared to scaffold alone or scaffold with only one GF (Patel et al. 2008).

Successful regeneration of large bone defects might also benefit from concomitant stimulation of vascularization and osteogenesis. Hence, we suggest that EPC and MSC based therapy might enhance both processes because these cells are capable of participating in vasculogenesis, might induce mesenchymal progenitors to proliferate or differentiate into osteoblasts and possibly at the same time gain plasticity to differentiate themselves into bone forming cells (Bick et al. 2006).

Identification of EPC is rather controversial and complicated since three different populations of EPCs were identified:
1. CFU—Hill—these EPCs have weak proliferative and vasculogenic activities;
2. Circulating angiogenic cells—these cells are obtained from adherent peripheral blood mononuclear cells (PB-MNC) and do not form colonies in culture. They are positive to: CD133, CD31, CD45 and VEGFR-2.
3. Late EPCs—these cells are derived from adherent PBMNC and form endothelial colonies after 3-4 week of culture. They are thought to play a major role in revascularization in adults; they are positive to CD34, CD144, VEGF-R2 but negative to CD133, CD45 and CD14 (Hirschi et al. 2008, Hur et al. 2004, Yoder et al. 2007).

The participation of EPC in bone repair was reported by some researchers. Lee et al. and Cetrulo et al. showed the participation of EPC in distraction osteogenesis model (Lee et al. 2009, Cetrulo et al. 2005). The injection of human CD34 progenitor cells into non healing femoral fracture in nude rats enhanced bone healing compared with control group. The addition of VEGF antagonist to this model impaired not only angiogenesis but also osteogenesis and led the authors to suggest that these cells have paracrine effect on bone forming cells. (Lee 2008, Fuchs 2009).

Transplantation of autologeus EPC into critical size gap in sheep tibiae revealed full bridging at 3 months in 6 out of 7 E PC-transplanted defects while non or minimal new bone formation was observed radiographically in 8 sham-operated defects (Rozen et al. 2009). These authors also suggested that the effect of EPC is not limited to vasculogenesis but that they are also capable to transform into bone cells. When sheep EPC were sub-cultured under osteogenic conditions they changed their morphology and formed nodular aggregates (1-2 mm diameter) following 1-2 weeks incubation and stained positively by von Kossa (vK), alizarin red (AR) and osteocalcin immunohistochemistry, which are markers of osteoblastic differentiation (Bick et al. 2006).

To be able to use cell-based therapy in animal and human defects a suitable scaffold is required that will not only serve as a vehicle for cellular delivery, but will also have osteoconductive properties. Tricalcium phosphates (TCP) is a synthetic scaffold used in the clinics for the reconstruction of bone defects. These materials provide a mineral matrix phase similar to that found in bone tissue. Following application, TCP is resorbed by osteoclastic activity and replaced by newly formed bone. Additionally, TCP as a synthetic material does not pose the risk of transmitting pathogenic agents (such is the case with allographs and xenographs). It is also being resorbed more rapidly when compared with a xenograft. (Rojbani H, Nyan M, Ohya K, Kasugai S. Evaluation of the osteoconductivity of a-tricalcium phosphate, β-tricalcium phosphate, and hydroxyapatite combined with or without simvastatin in rat calvarial defect. J Biomed Mater Res A. 2011 Sep. 15; 98(4):488-98.

By combining TCP with GBR we achieved a mean height of 5.5±0.24 mm new hard tissue under the capsule, significantly higher than bone formed when capsules were filled with Bio-Oss collagen (p<0.001). Histological analysis revealed that TCP was partially resorbed and replaced by new bone that was continuous with the original calvaria. Residual TCP particles were surrounded by vascularized dense connective tissue.

SUMMARY OF THE INVENTION

It is an objective of the present invention to provide a method for extra cortical bone augmentation by combining Guided Bone Regeneration (here in after GBR) techniques with implementation of progenitor/stem cells. It was discovered that the angiogenic effect of Endothelial Progenitor Cells (here in after EPC), combined with effects of space creation, clot stabilization and cell exclusion achieved by GBR, facilitates a predictable bone augmentation. Guided Bone Regeneration (GBR) techniques, known in the art, include space maintaining, blood clot stabilization and exclusion of epithelial as well as connective tissue cells. In combination with progenitor cells that participate in various stages of bone regeneration has shown a better and more predictable bone augmentation compared with GBR. The effect of bone marrow derived mesenchymal stem cells (hereinafter BM SC), peripheral blood derived endothelial progenitor cells (EPC) and the combination of both on bone augmentation using a GBR model, in rats' calvaria, has been studied.

It is another objective of the present invention to provide a method for extra cortical bone augmentation while maintaining the following constituent factors, in order to achieve predictable bone regeneration.

It is yet another objective of the present invention to provide a method of evaluating a predicted efficacy of extra cortical vertical bone augmentation method, by combining GBR technique and implantation of stem/progenitor cells, thereby providing a prognosis to particular potential patient.

It should be understood, however, that the eclectically synopsized brief summary supra is not to limit the invention to the particular forms and examples, but on the contrary, is to cover all modifications, equivalents, and alternatives falling within the scope of the invention.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

In accordance with some embodiments, the method of forming an extra cortical osseous tissue augmentation is achieved by maintaining the following constituent factors, in order to achieve predictable bone regeneration. The constituent factors to be maintained are:

1—An angiogenesis, to provide necessary blood supply and undifferentiated mesenchymal progenitor cells, which is typically achieved by (EPC);

2—Space maintenance, to facilitate adequate space for bone ingrowth, and shaping of the newly formed osseous tissue, typically achieved by (GBR);

3—To provide stability of wound and/or implant to induce initial blood clot formation and uneventful healing events.

In accordance with some embodiments, the method of forming an extra cortical osseous tissue, using GBR and scaffolding, includes the following steps. Initially the portion of the surface of the bone the augmentation of which is desired is exposed. Thereafter, optionally using a dental hand-piece, small perforations of the cortical bone are preformed, preferably under cooling conditions, e.g. while rinsed with saline water. This is in order to allow blood clot formation and cells and nutrients passage from the endosteum (Lundgren et al. 2000).

To achieve the synergistic effect induced by MSC, EPC and/or MSC with EPC sells, a tissue culture thereof is seeded on the scaffolding. Cells are typically seeded on the scaffold 1 day before the transplantation. Following the perforation of the bone, scaffolds seeded with stem/progenitor cells will be placed on the decorticated bone. The cells are extracted and cultured in accordance with the procedures exemplified infra.

Scaffolding is then placed on the decorticated bone. Preferably a rigid gold enclosure is fixed to the underling bone, typically using gold screws, so as to surround the decorticated portion bone, the augmentation of which is desired. Optionally the surgical flap is repositioned and sutured with resorbable sutures to achieve primary wound closure.

The rigid enclosure is removed and the calvarium+scaffold is optionally evaluated. Afterwards, histological evaluation and immune-stainings is optionally performed on the same specimens.

In accordance with some embodiments, the method of evaluating a predicted efficacy of extra cortical vertical bone augmentation method, by combining GBR technique and implantation of stem/progenitor cells, thereby providing a prognosis to particular potential patient, includes:

1—Isolating, culturing and characterizing stem and/or progenitor cells, including:
  (a) MSC from bone marrow;
  (b) EPC from peripheral blood.

2—Evaluating, typically supra crestal, bone formation using GBR technique in combination with stem and/or progenitor cells, including:
  (a) Test the adjunctive effect of BM MSC implantation to GBR.
  (b) Test the adjunctive effect of EPC implantation to GBR.
  (c) Test the adjunctive effect of EPC & MSC implantation to GBR.

3—Follow maturation, ossification and stability of the newly formed bone.

EXAMPLES

Surgical Procedure

Lewis rats were anaesthesized using Ketamin 10 mg/100 gr BW and Xylasin 0.5 mg/100 gr BW IM. Subcutaneous antibiotics (Cefalexin, 0.3 ml) and analgesic (Turbogezic, 0.3 ml) will be injected pre-operatively. Followed by U shape incision (FIG. 4A), a full thickness flap has exposed the parietal bone. Using a dental hand-piece, small perforations of the cortical bone were preformed under cooling conditions with saline water. This is in order to allow blood clot formation and cells and nutrients passage from the endosteum (Lundgren et al. 2000).

Figure 5A:
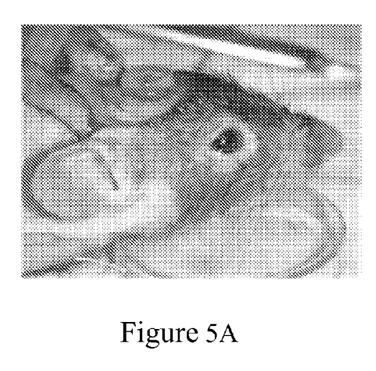
FIG. 5A shows control—cortical perforations+scaffold+capsule.
Figure 5B:
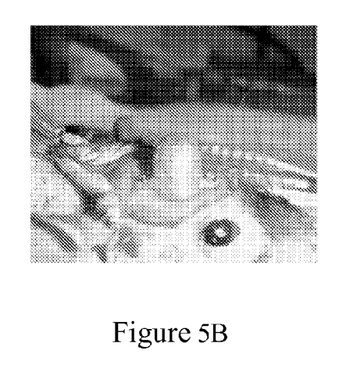
FIG. 5B shows test—cortical perforations+scaffold+capsule.

Scaffold was placed on the parietal bone. A rigid gold capsule (custom made: 5 mm height; 7 mm radius) was fixed to the underling bone using gold screws (as shown in FIG. 5B). The surgical flap was repositioned and sutured with resorbable sutures to achieve primary wound closure.

During the healing period, rats were fed rat chow and water ad libitum. Rats were sacrificed after 2 months. The calvaria with the capsules was fixed in 10% buffered formalin for 2 days and then immersed in 70% ethyl alcohol. The gold capsules were removed and the calvarium+scaffold will be scanned by CT. Afterwards, histological evaluation and immune-stainings were performed on the same specimens.

The adjuvant effects of rats' MSC, EPC and/or MSC with EPC cells seeded on scaffold to on GBR bone augmentation was achieved by seeding the cells on the scaffold 1 day before the transplantation. The surgical procedure was as described hereinabove. Following perforation of the parietal bone, scaffolds with stem/progenitor cells were placed on the bone. A rigid gold capsule was fixed to the underlining bone tissue using gold screws.

Augmentation of Parietal Bone in Rats by Human EPC Cells

Human EPC (hEPC) obtained from peripheral blood were isolated and characterized. 27 nude rats were divided into 4 groups: GBR+hyaluronic acid-fibrinogen scaffold (GS), GBR+scaffold+hEPC(GSC), scaffold+hEPC(SC) and scaffold alone(S). Following the exposure and perforation of the parietal bone, in the S and SC groups, scaffold with or without $10^5$ cells was laid on the bone. In the GS and GSC groups scaffold with or without $10^5$ cells was laid on the bone and covered by a rigid capsule. Rats were sacrificed 8 weeks later, and specimens were prepared for histological analysis.

The newly formed bone was quantified by measuring the maximal vertical bone height in the histological sections. The vertical bone height ranged from 1 to 5.13 mm. In the S+SC group, cortical perforations were completely healed; nevertheless, bone did not regenerate vertically. Mean maximal vertical bone height was similar to the width of the original calvaria (1.49±0.26 mm, 1.5±0.11 mm respectively). In the GS group, the regenerated bone was continuous with the calvaria and covered by periostum. The bone appeared mature with a mean vertical bone height of 2.88±0.61 mm. In the GSC group, results were similar to the GS group (2.18±0.25 mm). Bone height was almost double in the GBR groups; nevertheless hEPC did not enhance bone formation.

Additional studies are required in order to explore the effect of other stem/progenitor cells and different scaffold on bone formation in this model.

Isolation and Expansion of Rats' Bone Marrow Cells

Figure 1:
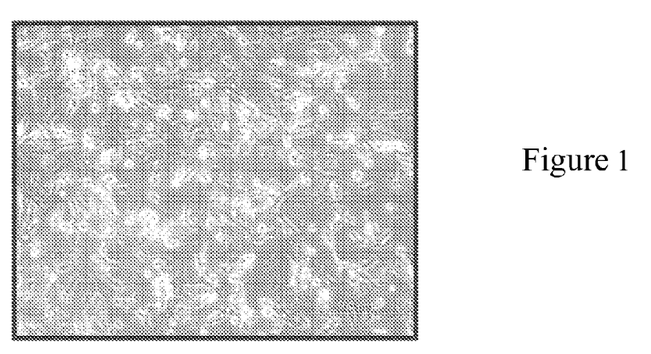
FIG. 1 shows spindle shape Lewis rat BM cells, 14 days after isolation.

Bone marrow from rats' tibiae was flushed, centrifuged at 250 g for 15 minutes and pelleted cells were seeded on culture dishes with DMEM (Dulbecco Modified Eagle's Medium) containing 10% FCS (Fetal Calf Serum) and 100 U/ml Pen-Strep. Cells were grown at 37° C. with humidified 95% air/5% $CO_2$, fed 3 times per week, split when confluent by brief trypsinization using 0.5% trypsine/0.2% EDTA (Biological Industries Ltd., Beit Haemek, Israel) and dispersed (FIG. 1).

Osteogenic differentiation of MSC was performed as follows, expanded MSC were grown in osteogenic differentiation media—DMEM/F12 (1:1) containing 10% FCS, Dexamethasone $10^{-7}$ M, ascorbic acid $5\times10^{-5}$ M and β-glycerophosphate 10-2 M. Osteoblastic differentiation was identified by nodule formation that were further characterized by alizarin red.

Figure 2:
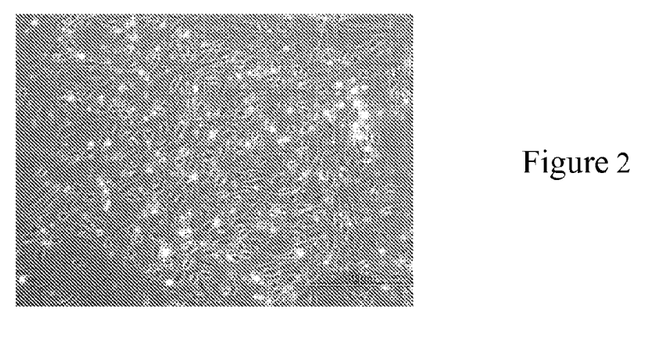
FIG. 2 shows peripheral blood derived Lewis rat cells, 7 days after isolation.

Isolation and Expansion of Blood Derived Rats' EPC 40 ml blood was drown from the heart of 5 Lewis rats. The Mononuclear fraction was isolated using Lymphoprep™ (Axis-Shield, Oslo, Norway), seeded on fibronectin (Sigma-Aldrich, MS, USA)-coated plates, and cultured in EBM-2 media supplemented with EGM-2MV SingleQuote (Clonetics, Cambrex Bio Science, MD, USA), containing 20% heat inactivated fetal bovine serum, vascular endothelial growth factor (VEGF), fibroblast growth factor-2, epidermal growth factor, insulin-like growth factor-1 and ascorbic acid. Cells were grown at 37° C. with humidified 95% air/5% $CO_2$. After 4 days of culture, non-adherent cells were discarded by gentle washing with PBS, and fresh medium were applied. The attached cells were continuously cultured with complete EGM-2 medium. Cells were fed 3 times per week, split when ~80% confluent by brief trypsinization and dispersed. FIG. 2 show peripheral blood derived Lewis rat cells, 7 days after isolation.

Figure 3:
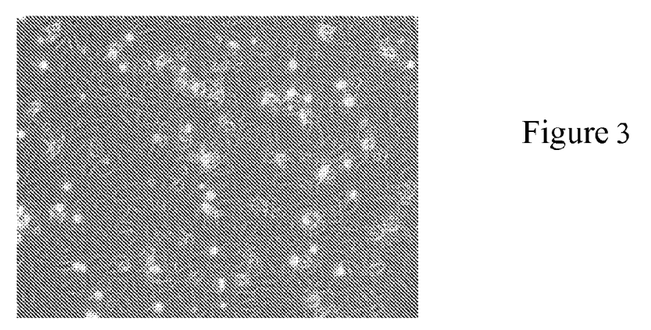
FIG. 3 shows cobble stone peripheral blood derived human late EPC, 25 days.

Isolation and Characterization of Peripheral Blood Derived Human Late EPC 50 ml blood were drawn from 25-35 years old healthy volunteers (Helsinki no. 2423) and human late EPC were isolated as described for rIEPC. FACS analysis found that >95% of the cells are positive for CD31, CD105 and CD 146, >70% for Tie-2, 30-40% for CD34, but importantly all of them are negative to CD14, ruling out their monocytic origin and supporting their angioblastic origin (FIG. 3).

Flow Cytometry Analysis (FACS)

Aliquots (5 $10^5$ cells) of lewis rat BM derived MSCs at Passages 1 to 3 were used for an analysis of cell-surface molecules. The cells were subcultured (as described earlier), resuspended in fluorescence-activated cell sorter (FACS) buffer consisting of 2% bovine serum albumin and 0.1% sodium azide (Sigma Chemical Co., St. Louis, Mo.) in PBS, and stained with fluorochromeconjugated mouse anti-rat CD90, CD45, CD44 (Antibodies Direct Serotec, Kidlington, UK), monoclonal antibodies according to the manufacturers' recommendations using mouse IgG1 monoclonal isotype antibodies to detect any nonspecific binding fluorescence (negative control). The cells were washed with PBS, resuspended in 0.5 mL FACS buffer, and analyzed for the expression of the aforementioned rat antigens using FACScan and CellQuest software for data collection and analysis (both from Becton Dickinson and Co., Franklin Lakes, N.J.). Gating was set to 1% or less of isotype-stained cells (IgG1 or IgG2).

TCP coating with fibronectin β-Tricalcium was performed as follows, phosphate scaffold (TCP)—Ossaplast®, (Osacure, Germany) was coated in fibronectin solution (Biological Industries Ltd., Beit Haemek, Israel) in order to enhance cell adhesion to the scaffold (26). On the day of surgery, 0.2 gr TCP granules were placed as a dense monolayer in 24 well plate and soaked in 100 microliter PBS mixed with 50 microliter fibronectin solution (5 micro gr/cm2) and incubated for 60 min.

Vertical Bone Augmentation Using GBR in Rats' Calvaria

Figure 4A:
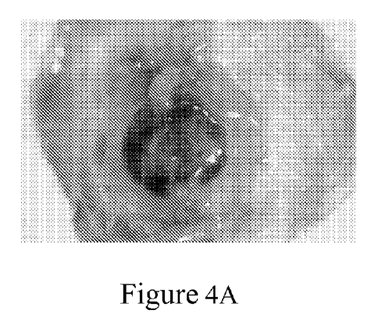
FIG. 4A shows macroscopically observed partially filling the space under the capsule.
Figure 4B:
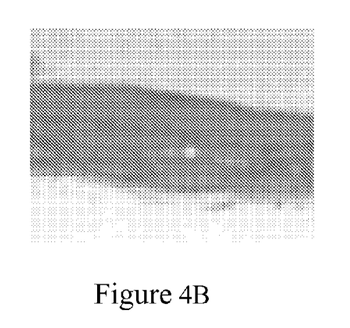
FIG. 4B shows histological analysis showing mature lamellar bone.

For establishment of a GBR in rats' calvaria, 2 Lewis rats were anaesthesized using Ketamin 10 mg/100 gr BW and Xylasin 0.5 mg/100 gr BW IM. Subcutaneous antibiotics (Cefalexin, 0.3 ml/300 gr BW) and analgesic (Turbogezic, 0.3 ml/300 gr BW) were injected pre-operatively. Followed by U shape incision, a full thickness flap exposed the parietal bone. Small perforations of the cortical bone were preformed under cooling conditions with saline water using a dental hand-piece and a diamond burr. A rigid 7 mm diameter, 5 mm height gold dome were fixed to the perforated bone (using fixation screws) which created and preserved a space underneath. The capsule was covered by the flap that was sutured with resorbable sutures. Rats were fed rat chow and water ad libitum. Two months later, rats were sacrificed and capsules were retrieved. Limited vertical bone, only partially filling the space under the capsule, was observed macroscopically (FIG. 4A). Calvaria were fixed in 10% buffered formalin for 2 days and then immersed in 70% ethyl alcohol. Thereafter, bones were decalcified in Calci-Clear Rapid, (national diagnostic, Atlanta, Ga., USA) and processed for paraffin embedding. Five pm sections were stained with H&E. Histological analysis showed mature lamellar bone (FIG. 4B).

The Effect of Early EPC and Hyaluronic Acid-Fibrinogen (HAF) Scaffold with or without Membrane Barrier on Vertical Bone Augmentation 27 nude rats (Hsd: RH-FoxN1$^{RNU}$, Harlan, Ind., USA) were enrolled in this experiment. 4 days before the experiment, 50 ml blood was obtained from human volunteers (Helsinki no. 2423). The mononuclear fraction was isolated using Ficoll-Paque™ Plus (GE Healthcare, US), seeded on extracellular matrix-coated plates and cultured in X-Vivo 15 medium (Biowhittaker, US) supplemented with human recombinant VEGFA (ReliaTech, GE). These cells were positive for CD31 and CD14 hence defined as early EPC. 150 μl HAF hydrogel scaffold (supplied by Procore Biotech Ltd.) was polymerized immediately before transplantation by addition of 50 μl thrombin (0.33 U/ml). Rats were anaesthesized and received pre operative antibiotics (Cefalexin) and analgesic (Turbogezic) as described above. The parietal bone was exposed and perforated. Rats were divided into 4 groups:
1) HAF—(n=3), 200 μl polymerized HAF were laid on the underling bone and allowed to polymerize (FIG. 5A).
2) GBR— (n=6), a gold capsule covered 200 μl polymerized HAF and fixed to the bone using fixation screws (FIG. 5B).
3) HAF & early hEPC (n=6), 200 μl polymerized HAF mixed with $10^5$ early hEPC was applied as in group 1. 4) HAF& hEPC & GBR— (n=12), $10^5$ early hEPC were mixed with 200 μl polymerized HAF and covered by a rigid capsule as described for the GBR group (2). Rats were kept in sterile conditions. Each nude rat was kept in a separate cage. After 8 weeks rats were euthanized by $CO_2$ asphyxation. Capsules were removed and the calvaria was fixed in 10% buffered formalin for 2 days and then immersed in 70% ethanol. A clear liquid was noticed under the capsules. Fixed bones were decalcified in Calci-Clear Rapid, (national diagnostic, Atlanta, Ga., USA) and processed for paraffin embedding. Five pm sections were stained with H&E.

Figure 5C:
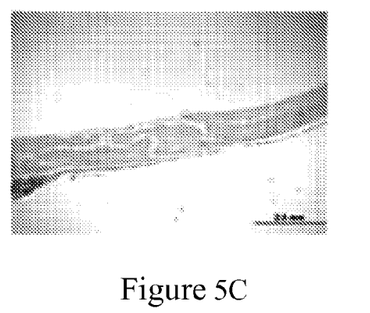
FIG. 5C shows control—cortical perforations+scaffold+capsule.
Figure 5D:
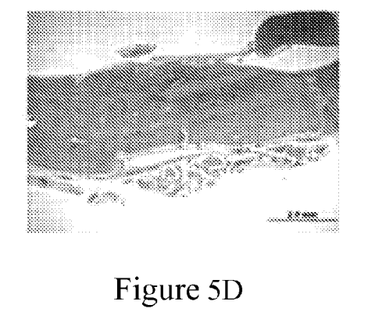
FIG. 5D shows test—cortical perforations+scaffold+capsule.

In the HAF group (1), cortical perforations were completely healed. Measurements of the maximal vertical bone height showed that the width of the bone is equal to that of the original rats' calvaria (1.49±0.26 mm) therefore, bone did not regenerate vertically (FIG. 5C). In the GBR group (2), the regenerated bone appears mature and reversing lines could be noticed. Mean vertical bone height was 2.88±0.61 mm (FIG. 5D). Thus GBR resulted in some bone regeneration.

Figure 5E:
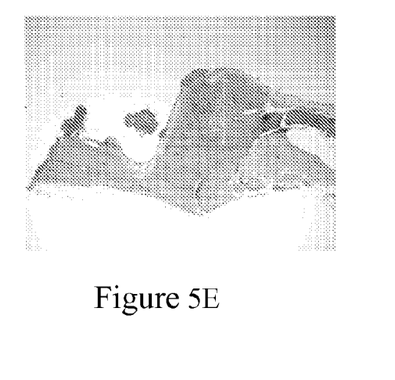
FIG. 5E shows test—decortications+scaffold+early Hepc+capsule.

In the HAF and hEPC group (3), the mean vertical bone height was almost similar to the original calvaria and to the HAF group 1 (1.5±0.11 mm) thus, early hEPC did not improve bone regeneration. Follow the addition of capsule (HAF+eariy hEPC+GBR) group (4), vertical bone formation was noticed (2.18±0.25 mm) similar to that observed in group (3) (HAF+GBR) again early hEPC had no adjunctive effect to bone augmentation (FIG. 5E).

Table 1 summarizes the results of this experiment:

|  | HAF | HAF + hEPC | HAF + GBR | GBR + HAF + hEPC |
|---|---|---|---|---|
| Mean maximal vertical bone height (±SE) | 10.49 ± 0.26 | 1.5 ± 0.11 | 2.88 ± 0.61 | 2.18 ± 0.25 |

Since GBR groups presented almost double vertical bone height compared with scaffold alone, this proves the importance of GBR to vertical bone regeneration. Thus rigid capsules are preferably to be installed in order to create a space for bone regeneration. Moreover, early EPC did not improve bone regeneration, therefore it is preferable to test the potential of late EPC and MSC to improve bone regeneration.

If the HAF scaffold is not available, 3 different scaffolds that are commonly used for bone augmentation: Bio-Oss collagen, collagen sponge and TCP were evaluated.

Vertical Bone Formation by GBR Using 3 Different Scaffolds 3 different scaffolds were explored for their effect on vertical bone formation by GBR. 9 in-bred Lewis male rats were divided into 3 experimental groups, namely:
1—Bio-Oss collagen group: 4×4×4 mm Bio-Oss collagen covered by a rigid capsule.
2—Collagen group: 4×4×4 mm collagen sponge covered by a rigid capsule.
3—TCP group: 0.25 gr of TCP granules covered by a rigid capsule.

Figure 6A:
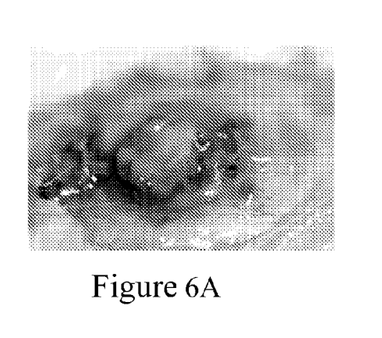
FIG. 6A shows clinical—collagen scaffold.
Figure 6B:
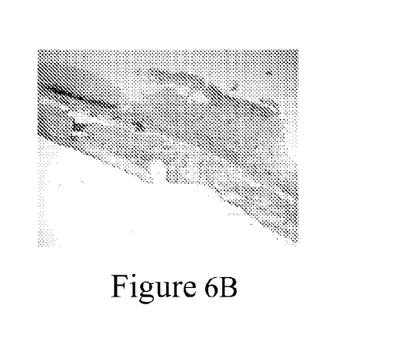
FIG. 6B shows histological—collagen scaffold.
Figure 8A:
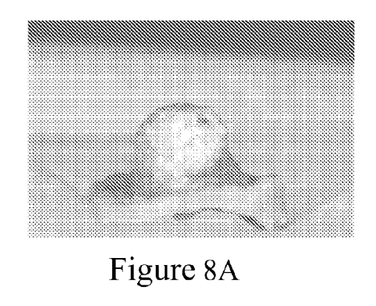
FIG. 8A shows clinical—TCP scaffold.

Surgery, scaffold implantation, anesthetics, pre-operative analgesics and antibiotic were administrated as previously described. Rats were sacrificed after 8 weeks by $CO_2$ asphyxation. After sacrifice, capsules were removed. In the TCP group the highest protuberances were noticed on the calvaria (FIG. 8A). All specimens were fixed in formalin for 2 days and then immersed in 70% ethyl alcohol. Fixed bones were decalcified in Calci-Clear Rapid, (national diagnostic, Atlanta, Ga., USA) and processed for paraffin embedding. Five pm sections were stained with H&E. The histological analysis revealed residual scaffold in all experimental groups. In the collagen group, the maximal vertical bone height was approximately 1.5 mm (FIGS. 6A clinical and 6B histological right view) and was covered by a thick (2-4 mm) fibrous tissue.

Figure 7A:
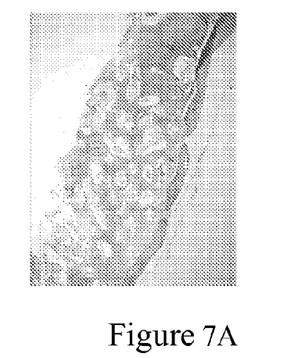
FIG. 7A shows Bio-Oss collagen scaffold residual scaffold particles.
Figure 7B:
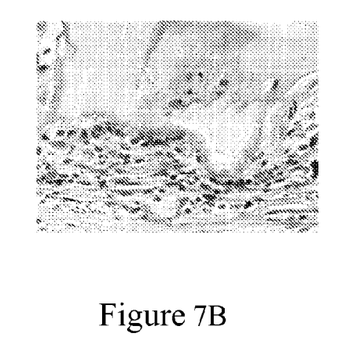
FIG. 7B shows Bio-Oss collagen scaffold particles are 4-5 mm height.

In the Bio-Oss collagen group the maximal vertical bone height was approximately 1.2 mm. Particles of the residual scaffold were encapsulated with highly infiltrated loose connective tissue (FIG. 7B) and were 4-5 mm height (FIG. 7A).

Figure 8B:
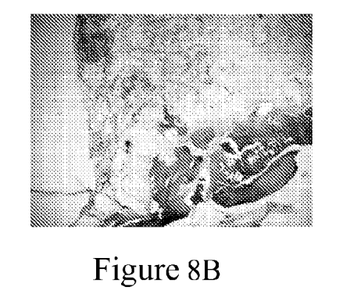
FIG. 8B shows histological—TCP scaffold.
Figure 9:
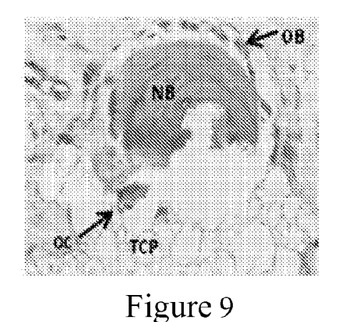
FIG. 9 shows TCP scaffold x40, NB=New bone proximity to TCP particles, OC=osteoclast; OB=osteoblast.

In the TCP group the maximal bone height was 2 mm in continuation with another 4 mm height of islands of dense connective tissue surrounding the residual scaffolds with numerous areas of new lamellar bone (FIGS. 8A clinical and 8B histological right views). Osteoclasts were observed near the TCP particles coupled with osteoblasts and new bone (FIG. 9).

According to the results of this feasibility experiment, TCP scaffold showed the highest potential for bone regeneration. Therefore, the TCP scaffold is expected to provide the foremost clinical benefit. Since most of the newly formed tissue was immature (after 8 weeks), it is preferable to terminate the regeneration phase after 2 or 3 months.

Vertical Bone Augmentation Using GBR and Cell Transplantation

Three combinations of progenitor cells and scaffold were transplanted under a rigid capsule in rats' calvaria, These included:
1) Bone marrow derived MSC (bmMSC)
2) Osteogenic transformed MSC (otMSC)
3) Peripheral blood derived progenitor cells (PBPC)

Male Lewis Rats (approximately 300 g) were allocated into 4 experimental groups: Group I $5\times10^5$ bmMSC (n=5); Group II, $5\times10^5$ otMSC (n=7); Group III, $5\times10^5$ PBPC (n=5); Group IV, control (C) TCP (n=4). Surgery, scaffold implantation, anesthetics, pre-operative analgesics and antibiotic were administrated as previously described. Rats were sacrificed after 8 weeks by CO2 asphyxation. Before transplantation $5\times10^5$ cells (suspended in 1 micro-liter medium) were mixed with 0.2 gr fibronectin coated PTCP particles and filled rigid gold domes (7 mm radius, 5 mm height).

The Domes were fixed to the calvaria using fixation screws that were attached in its anchoring rings. The flaps were repositioned and sutured, with minimal tension, using resorbable sutures. Immediately post-op and during the whole experiment, each rat was kept in a separate cage and all rats were fed rat chow and water ad librium. Result: After 3 months cells~doubled the mean maximal vertical bone height: EPC 4.02±0.3 mm, MSC 4.1±0.5 mm, otMSC 4.1±0.3 mm, compared with TCP (2.3±0.2 mm, n=4). Bone area fraction (%) was significantly increased in the EPC and otMSC compared with TCP (28.9±2.7 p=0.05, 28.9±2.0 p≤0.02, 21.4±1.1, respectively). Additional experiments are required to further improve vertical bone augmentation in order to achieve clinically significant bone height.

Histological preparations and histomorphomentric analysis Fixed bones were decalcified in Calci-Clear Rapid, (national diagnostic, Atlanta, Ga., USA) for 2-3 days and processed for paraffin embedding. Five pm sections were stained with H&E for determination of bone morphology. Scaffold degradation and inflammatory infiltration were graded as high, medium or low. For Histomorphometric measurements, 4 H&E stained slides (20μηι apart) from each specimen were captured by a computer camera (Olympus DP70) with a calibration scale. Three parameters were measured using image J software (image processing and analysis):
1) Vertical bone height: maximal height of the bone that was measured form the bottom of the calvaria to the crest of the bone.
2) Bone area—bone area under the dome. Since the newly formed bone could not be separate from the original calvaria, bone area includes: newly formed bone+original calvaria.
3) Bone fraction—percentage of bone within the tissue under the capsule.

Statistical analysis Sigma plot computer software was used for statistical analysis. Descriptive statistics included mean and standard error (SE) of the maximal vertical bone height and augmented tissue for each experimental group. In order to compare the bone height and augmented tissue dimensions between the groups, student un-paired t-test analysis was preformed. Results were regarded as significant at p<0.05.

Cell Expansion—PBPC and bmMSC

Total rat mononuclear cells (MNC) were seeded. Immediately after seeding cells appeared round, but after 3 to 5 days, attached cells appeared as elongated and spindle shaped. Following re-plating, they rapidly replicated from several cells to colonies and formed a monolayer of homogenous appearance. The cultured cell population was morphologicallypure and did not contain hematopoietic cells. Self renewal of cells was preserved for 7 passages.

In Vitro Osteogenic Differentiation of bmMSC

BM cells were positive for CD90 and CD44 and negative for CD

45. When grown in osteogenic conditions, nodule formations were seen and culture was positively stained for alizarin red.

Descriptive Histology and Histomorphometry Measurements

Histological slides revealed that the augmented tissue was composed of bone, residual scaffold and connective tissue. The proportion of these components were different among the experimental groups. In the lower part of the specimens newly formed compact bone was continuous with the original calvaria. Characteristics or mature lamellar bone were observed in most areas (e.g.: reversing lines, osteocyte trapped in empty lacuna) however in some areas woven bone was noticed (as demonstrated by picro-serius red. The upper (distal) part of the augmented tissue contained residual scaffold surrounded by dense vascularized connective tissue.

Histomorphometric measurements have resulted with following values. Vertical bone height ranged from 2.1-3.5 mm in the control group (mean 2.7±0.29 mm). Vertical bone height was approximately doubled following addition of cells (compared with control group): PBPC 4.07±0.26 mm (range 3.5-5.2 mm, p=0.01), MSC 4.1±0.54 mm (range 2.3-5.5 mm, p=0.07), otMSC 4.1±0.32 mm (range 3.1-5.8 mm, p≤0.01).

Bone area was highest in the otMSC group (mean 33.9±2.41 ranged from 23.7-40.7 mm2), and significantly different from control (mean 20.4±2.5 mm, range 13-24 mm2, p<0.005). Bone area in PBPC and bmMSC groups was almost similar and higher than control: mean 27.12±2.65 mm2 (bmMSC), 27.5±2.66 mm2 (PBPC). Bone area fraction was comparable in PBPC and otMSC groups (mean mean 28.9±2.7, 28.9±2.0 respectively) and higher than bmMSC and (C) (mean 23.4±2.6, 21.4±1.1 respectively). Statistical significance were observed between PBPC and otMSC groups and (C) (p=0.05 and p≤0.02, respectively).

In Vivo Experiment

All rats survived the surgical procedures and healing was un-eventful. Although the surgical sites had all healed per-primum, a focal necrosis of the skin overlying the capsule was noticed a month after the surgery. This caused spontaneous exposure of the capsules in 30% of the rats. Infection signs were not observed in the areas of the capsules' exposure and were therefore not treated. In one rat, the exposed capsule was exfoliated; this animal (from control group) was excluded from the experiment.

Clinical macroscopic view following removal of the capsule showed new augmented hard tissue filled the space under the capsule. This augmented tissue appeared non-homogenous and was composed of particulate residual scaffold material surrounded by new host tissue.

It will be appreciated by persons skilled in the art that the present invention is not limited by what has been particularly shown and described herein above. Rather the scope of the invention is defined by the claims which follow:

What is claimed is:

1. A method of facilitating augmentation of osseous tissue on a surface of a bone, said method comprising:
  (a) providing a scaffolding and a rigid enclosure;
  (b) preparing a surface of a bone for augmentation of osseous tissue, wherein said preparing comprising at least one of: exposing at least one portion of the surface where augmentation is desired; and performing a plurality of minute perforations in at least one cortical portion of said bone where augmentation is desired;
  (c) placing said scaffolding on the portions of said bone;
  (d) placing said rigid enclosure onto said scaffolding thereby enclosing said scaffolding relatively to the surface of said bone;
  (e) seeding cells on said scaffolding thereby obtaining a newly augmented osseous tissue on the surface of said bone wherein said cells are selected from at least one cell culture selected from the group consisting of: an early endothelial progenitor cell culture; an early mesenchymal stem cells culture; a late endothelial progenitor cell culture; a late mesenchymal stem cells culture; peripheral blood derived endothelial progenitor cells and mesenchymal stem cells.

2. The method of claim 1, wherein the cells are progenitor cells.

3. The method of claim 2, wherein said seeding is performed at most one day prior to enclosing.

4. The method of claim 2, wherein said scaffolding comprises at least one of a synthetic scaffolding, hyaluronic acid-fibrinogen scaffolding, collagen sponge type of scaffolding and TCP granules type of scaffolding.

5. The method of claim 2, wherein enclosing comprises providing an enclosure and enclosing said scaffolding relatively to the surface of said bone with said enclosure.

6. The method of claim 5, further comprising removing said enclosure thereby obtaining a newly augmented osseous tissue on the surface of said bone.

7. The method of claim 6, wherein removing is carried out within 1 to 9 months after enclosing said enclosure.

8. The method of claim 2, wherein said scaffolding is placed on a decorticated bone.

9. The method of claim 2, wherein said augmentation is vertical bone augmentation or an extra cortical bone augmentation.

10. The method of claim 5, wherein enclosing comprises fixing said enclosure to the bone, thereby surrounding said at least one portion of the bone.

11. A system for facilitating augmentation of osseous tissue on a surface of a bone, said system comprising:
  (a) a scaffolding adapted to be placed on a bone;
  (b) a rigid enclosure adapted to enclose said scaffolding; and
  (c) cells from at least one cell culture selected from the group consisting of: an early endothelial progenitor cell culture; an early mesenchymal stem cells culture; a late endothelial progenitor cell culture; a late mesenchymal stem cells culture; peripheral blood derived endothelial progenitor cells and mesenchymal stem cells, wherein said cells are seeded onto said scaffolding.

12. The system of claim 11, wherein said scaffolding is adapted to be placed on a bone comprising a plurality of minute perforations at the cortical portion of said bone.

13. The system of claim 11, wherein said scaffolding comprises at least one scaffolding selected from the group consisting of: synthetic scaffolding, hyaluronic acid-fibrinogen scaffolding, collagen sponge type of scaffolding and TCP granules type of scaffolding.

14. The system of claim 11, wherein said rigid enclosure is adapted to be fixed onto a surface of a bone.

15. The system of claim 11, wherein said scaffolding is adapted to be placed on a decorticated bone.

16. The system of claim 11, wherein said system facilitates vertical bone augmentation or an extra cortical bone augmentation.

17. A method of facilitating augmentation of osseous tissue on a surface of a bone using the system of claim 11, wherein the method comprises the steps of:
   preparing a surface of a bone for augmentation of osseous tissue, wherein said preparing comprising at least one of: exposing at least one portion of the surface where augmentation is desired; and performing a plurality of minute perforations in at least one cortical portion of said bone where augmentation is desired;
   placing said scaffolding on the portions of said bone;
   enclosing said scaffolding relatively to the surface of said bone by placing a rigid enclosure onto said scaffolding;
   seeding the cells on said scaffolding thereby obtaining a newly augmented osseous tissue on the surface of said bone, wherein the cells are progenitor cells.

* * * * *